United States Patent [19]

McNamara et al.

[11] Patent Number: 6,004,347
[45] Date of Patent: Dec. 21, 1999

[54] NON-MIGRATING VASCULAR PROSTHESIS AND MINIMALLY INVASIVE PLACEMENT SYSTEM THEREFOR

[75] Inventors: Edward I. McNamara, Chelmsford; Michael F. Weiser, Groton, both of Mass.

[73] Assignee: C. R. Bard, Inc., Murray Hill, N.J.

[21] Appl. No.: 08/760,360

[22] Filed: Dec. 4, 1996

Related U.S. Application Data

[63] Continuation of application No. 08/051,728, Apr. 22, 1993, abandoned.

[51] Int. Cl.$^6$ ............................................. A61F 2/06
[52] U.S. Cl. ........................... 623/1; 606/198; 606/194; 623/11
[58] Field of Search ............................. 604/104, 105, 604/106; 606/191, 192, 194, 198, 199, 200; 623/1, 11

[56] References Cited

U.S. PATENT DOCUMENTS

| | | |
|---|---|---|
| 3,657,744 | 4/1972 | Ersek . |
| 3,703,896 | 11/1972 | Nuwayser . |
| 4,140,126 | 2/1979 | Choudhury . |
| 4,560,374 | 12/1985 | Hammerslag . |
| 4,562,596 | 1/1986 | Kornberg . |
| 4,577,631 | 3/1986 | Kreamer . |
| 4,580,568 | 4/1986 | Gianturco . |
| 4,617,932 | 10/1986 | Kornberg . |
| 4,740,207 | 4/1988 | Kreamer . |
| 4,830,003 | 5/1989 | Wolff et al. . |
| 4,994,071 | 2/1991 | MacGregor . |
| 4,994,077 | 2/1991 | Dobben . |
| 5,035,706 | 7/1991 | Gianturco et al. . |
| 5,064,435 | 11/1991 | Porter .................... 606/151 |
| 5,207,695 | 5/1993 | Trout, III .................. 623/1 |
| 5,234,447 | 8/1993 | Kaster et al. .............. 606/151 |
| 5,275,622 | 1/1994 | Lazarus et al. ............. 623/1 |
| 5,330,500 | 7/1994 | Song ........................... 623/1 |
| 5,360,443 | 11/1994 | Barone et al. ............. 623/12 |
| 5,456,713 | 10/1995 | Chuter ...................... 606/194 |
| 5,489,295 | 2/1996 | Piplani et al. .............. 623/1 |
| 5,741,333 | 4/1998 | Frid .......................... 623/12 |

FOREIGN PATENT DOCUMENTS

| | | |
|---|---|---|
| 0421729 | 4/1991 | European Pat. Off. . |
| 0466518 | 1/1992 | European Pat. Off. . |
| 1217402 | 3/1986 | U.S.S.R. . |
| 1318235 | 6/1987 | U.S.S.R. . |
| 1457921 | 2/1989 | U.S.S.R. . |
| WO8908433 | 9/1989 | WIPO . |

OTHER PUBLICATIONS

Rollins et al., "Self–Expanding Metallic Stents: Preliminary Evaluation . . . ", Radiology, Jun. 1987, pp. 739–742.

Mirich et al., "Percutaneously Placed Endovascular Grafts for Aortic Aneurysms . . . ", Radiology, Mar. 1989, pp. 1033–1037.

Lawrence, Jr. et al., "Percutaneous Endovascular Graft: Experimental Evaluation", Radiology, May 1987, pp. 357–360.

Dobben et al., "Prostatic Urethra Dilatation with the Gianturco Self–Expanding Metallic Stent . . . ", AJR, Apr. 1991, pp. 757–761.

*Primary Examiner*—Paul B. Prebilic
*Attorney, Agent, or Firm*—Arthur Z. Bookstein

[57] ABSTRACT

A graft assembly for securely position a graft at a predetermined location across an abdominal aortic aneurysm. The assembly includes a resilient self expanding anchor that is secured to the distal end of a mesh graft. The anchor is formed from a single wire having a series of zigzag bends, such that when the ends of the wire are attached a tubular anchor is produced. The anchor is further characterized by curved segments between the bends which a create an anchor having a reverse barrel shape.

21 Claims, 8 Drawing Sheets

NON-MIGRATING VASCULAR PROSTHESIS AND MINIMALLY INVASIVE PLACEMENT SYSTEM THEREFOR

This is a continuation of application Ser. No. 08/051,728, filed Apr. 22, 1993 now abandoned.

FIELD OF THE INVENTION

The invention relates to devices and techniques for placing and securing a vascular graft in a predetermined location in a patient's vascular system.

BACKGROUND OF THE INVENTION

It has been long accepted practice to treat a variety of vascular disorders in a surgical procedure that involves placement of a vascular graft in a patient's vascular system. The construction and characteristic of the graft typically will be adapted to optimize its use in the specific surgical environment and condition to be treated and, accordingly, a number of different types of grafts are available. Among the most common types of vascular grafts are those formed from a woven or knitted tubular fabric as well as non-fabric tubes such as expanded polytetrafluoroethylene. Such grafts typically are placed in a patient's vascular system in a highly invasive surgical procedure. In general, the complexity of the surgical procedure required to place the graft will depend on many factors, including the location and surgical accessibility of the portion of the patient's vasculature where the graft is to be placed.

Not all vascular conditions in which it would be desirable to place a graft can be so treated. Among the particularly troublesome medical conditions in which it is desirable to place a graft is that of an abdominal aortic aneurysm, in which a portion of the patient's aorta, the major artery carrying blood from the heart, has developed a weakened wall such that the weakened portion will tend to expand under the influence of the patient's blood pressure. An aortic aneurysm presents a life threatening risk that the aneurysm may burst causing massive internal bleeding. Treatment of the condition typically has involved deeply invasive abdominal surgery in which the patient's abdominal cavity is opened to reach and expose the aortic aneurysm. While maintaining the patient on an independent life support system, the region of the aneurysm is incised lengthwise to enable insertion of the graft into the aorta to span the weakened region and define a structurally round flow path between the remaining healthy portions of the aorta. The graft so positioned then is sutured in place. The graft thus serves as a reinforcing liner for the weakened portion of the aorta. Such surgical procedures have been characterized by a relatively high mortality rate. Typically, patients suffering from the condition are elderly and are less able to survive the rigors of major abdominal surgery. Additionally, there is a substantial degree of risk when the abdominal cavity is opened because the confining pressure of other abdominal organs on the aorta is released. In some cases, the abdominal wall in the region of the aneurysm is so weak that upon release of the confining pressure, the aneurysm bursts with resulting immediate massive hemorrhaging.

It would be desirable, therefore, to provide an apparatus, system and technique for placement of a graft, such as, but not limited to, placement in the abdominal aortic region, with a less invasive procedure that presents less risk to the patient. It is among the general objects of the invention to provide such a system.

BRIEF DESCRIPTION OF THE PRIOR ART

Mirich et al., in "Percutaneously Placed Endovascular Grafts for Aortic Aneurysms: Feasibility Study", *Radiology* (March 1989), describes the use of nylon covered, self expanding metallic stents to repair abdominal aortic aneurysms that were artificially produced in dogs. Mirich et al. describes a graft framework constructed from three self expanding metallic zigzag stents connected in tandem. The two lower stents are covered with nylon. The graft is anchored in position by barbs attached to both ends of the graft. Delivery of the framework is achieved by compressing the nylon covered graft and advancing it through a catheter with a blunt tipped introducer wire. When the nylon covered portion of the graft bridges the aneurysm, the introducer wire is held in place and the catheter slowly withdrawn. This releases the graft assembly and allows the stents to expand until they press against the vessel walls.

In a similar procedure, Lawrence Jr. et al., in "Percutaneous Endovascular Graft: Experimental Evaluation", *Radiology* (May 1987), discloses the use of an expanding stent of the type disclosed in U.S. Pat. No. 4,580,568 (Gianturco) to anchor and support a Dacron graft. The Gianturco stent comprises a wire formed into a closed zigzag configuration by creating an endless series of straight sections joined by bends. The stent is resiliently collapsible into a smaller generally tubular, low profile shape. In its compressed, low profile shape, the straight sections are arranged side-by-side, in close proximity, to facilitate insertion. The stent is resiliently expandable such that the straight sections press against the wall of the artery to maintain it open when the stent is permitted to resiliently expand.

The procedure disclosed by Lawrence Jr. et al. includes the use of a plurality of Gianturco stents in tandem. Dacron tubing is wrapped around the outside of the middle group of the stents, internalizing the stents within the graft. As a result, the lead and trail stents act as anchors, while the internal stents served to open the tubular graft when the device is released from the catheter. As with the procedure disclosed by Mirich et al., a catheter is used to deliver the graft framework to the treatment site.

The use of expanding stents is discussed further by Dobben et al. in "Prosthetic Urethra Dilatation with the Gianturco Self-expanding Metallic Stent: A Feasibility Study in Cadaver Specimens and Dogs", AJR 156:757–761 (April 1991). Dobben et al. describes the use of stainless steel stents bent into a zigzag pattern and then formed into a cylinder. Stents having flared ends as well as stents that are not flared are discussed. The stents are said to have been delivered to a predetermined location by using a coaxial Teflon introducer system. The flared stents were said to have been flared outwardly at both ends, and, when fully expanded, had a smaller diameter in the center than at the ends.

SUMMARY OF THE INVENTION

The present invention relates to a device, system and technique for the minimally invasive, percutaneous placement of a vascular graft, such as in the repair of an abdominal aortic aneurysm. The device includes a tubular synthetic graft having proximal and distal ends. When placed, the graft is held in position in the blood vessel by one or more resilient, self expanding anchors. The anchor is formed from a single, continuous wire bent in a zigzag configuration to define a series of elongate wire segments connected by bends. The anchor defines a three-dimensional generally tubular structure having proximal and distal ends. The anchor is compressible to a low profile (small diameter) and can expand resiliently to an enlarged diameter.

In one aspect of the invention, curved wire segments of the anchor define somewhat of an hourglass configuration in which the midportion of the generally tubular anchor defines a narrowed waist that is smaller in diameter than at the ends. The anchor is attached to an end of the tubular synthetic graft. The diameter of the fully expanded graft preferably may be less than the fully expanded, relaxed diameter of the anchor so that when an end of the anchor is attached to the graft, the graft will open fully. The end of the anchor that is attached will be contracted somewhat, thereby accentuating the radially outward curvature of the other (distal) end of the anchor. The distal end of the anchor thus is adapted to bear against the wall of the blood vessel at a plurality of points (in the region of the bends) rather than along the full length of the wire segments. By so concentrating the point of contact of the anchor with the blood vessel, a more secure attachment of the anchor to the vessel wall is achieved thereby reducing the risk of the device migrating downstream in the blood vessel.

In another aspect of the invention, the curved configuration of the wire segments is such that the attached (proximal) end of the anchor can be attached to the distal end of the synthetic graft in a manner that provides for a relatively smooth transition between the two. By minimizing the extent to which portions of the anchor protrude radially inwardly into the graft, the cross-sectional area of the lumen through the graft is not compromised. This is desirable, for example, should it be necessary to subsequently treat the patient with a catheter that must be passed through the graft. The absence of radially inwardly protruding anchor portions reduces the risk that the subsequently introduced catheter or other vascularly insertable member might become caught on the anchor.

Although the anchor may be attached to the graft by sutures, in a further aspect of the invention, it is preferred to capture a marginal end portion of the graft within a pair of wires that define a portion of the anchor. The wire portions may be welded together in a manner that captures a marginal end portion of the graft without the use of bulky sutures.

Attachment of the anchor to the vessel wall may further be enhanced by one or more radially outwardly protruding hooks attached to the wire segments. The hooks engage the vessel wall under the influence of the resilient anchor and enhance the anchor's resistance to migration once the graft is properly positioned. The hooks preferably are formed on the end of short segments of wire that are welded to the anchor to locate the hooks at regions adjacent to the distal bends. The hooks extend a short distance beyond the bends and become engaged in the blood vessel wall once the anchor is expanded.

The graft assembly is delivered percutaneously with a catheter-like delivery device that includes an outer sheath and an inner positioning member that extends through the outer sheath. The graft assembly is compacted to its low profile configuration and is loaded within the distal end of the sheath. The delivery device then is advanced into the patient's vascular system in an over-the-wire technique. The positioning member has a hollow lumen adapted to receive the guidewire. When the delivery system and graft assembly have been advanced to the intended site of deployment, the positioning member is held stationary while the sheath is withdrawn. As the sheath withdraws, the anchor and graft are progressively exposed so that the anchor can expand and resiliently engage the wall of the blood vessel.

It is among the general objects of the invention to provide an improved percutaneously deliverable vascular prosthesis that avoids post implantation migration.

Another object of the invention is to provide an improved system and technique for more securely anchoring and positioning the vascular graft within a blood vessel.

A further object of the invention is to provide an improved technique for treating a vascular aneurysm.

Another object of the invention is to provide a percutaneously placeable graft assembly that includes a graft and a resiliently expandable anchor attached to the graft in which the anchor is configured to concentrate the expansion force developed by the anchor at a plurality of discrete locations.

Another object of the present invention is to provide an improved method of securing the graft to the anchor.

BRIEF DESCRIPTION OF THE DRAWINGS

The foregoing and other objects and advantages of the invention will be appreciated more fully from the following further description thereof, with reference to the accompanying drawings wherein.

DETAILED DESCRIPTION OF THE INVENTION

Figure 1:
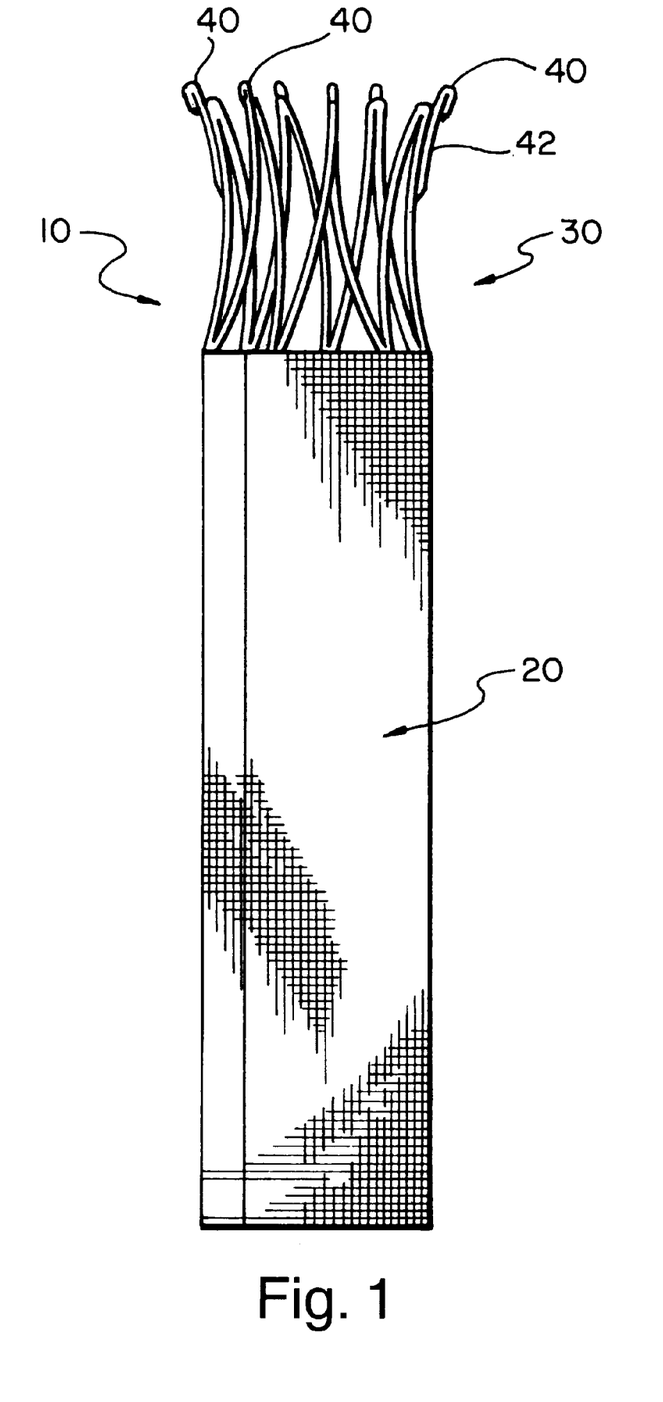
FIG. 1 is a side elevation of one embodiment of the graft assembly.

FIG. 1 illustrates one embodiment of a graft assembly, indicated generally at 10, adapted for use in the present invention. The assembly 10 includes a synthetic vascular graft 20 that is intended to be placed within a patient's blood vessel, the invention being described, for example, in connection with the treatment of an abdominal aneurysm. The graft 20 is tubular and may be formed from materials and in any of a variety of constructions known in the art. For example, the graft may be formed from expanded polytetrafluoroethylene with a porosity and internodal distance similar to grafts presently commercially available. Alternately, the graft may be formed from a fabric material, either woven or knitted, or in other configurations known in the art. Preferably, the graft has a porosity that will exhibit the desired properties of promoting tissue ingrowth while precluding undesired blood leakage. The graft preferably is provided with one or more radiopaque stripes to facilitate fluoroscopic or X-ray observation of the graft. The stripes may be formed in the graft by any conventional means as will be appreciated by those skilled in the art. The assembly 10 also includes an anchor 30 that is secured to the distal end of the graft and serves to retain the graft in position in the blood vessel.

Figure 2:
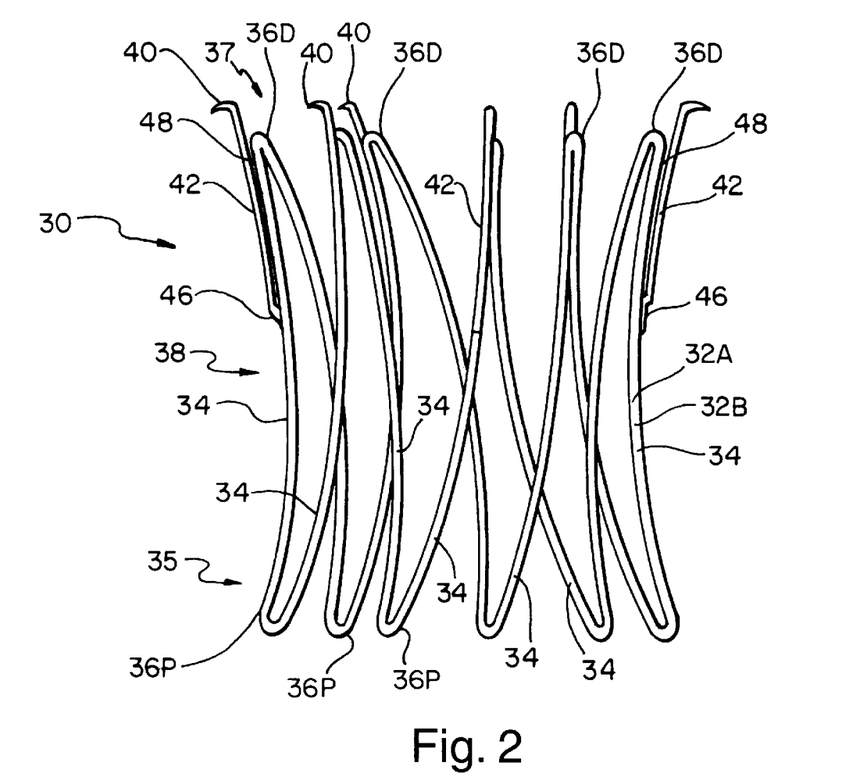
FIG. 2 is an enlarged elevation of the anchor shown in the graft assembly of FIG. 1.

FIG. 2 shows, somewhat diagrammatically, the anchor 30. The anchor 30 may be made from a single continuous length of metal wire. The wire preferably may be an alloy of nickel (35%), cobalt (35%), chromium (20%), and molybdenum (10%). Such wire is available from Maryland Specialty Wire Company, Cockeysville, Md. under the trade designation MP35N. The alloy has high corrosion resistance, is non-magnetic and has a strength comparable to stainless steel. The wire is formed to define a series of wire segments 34 and alternating proximal and distal bends 36P, 36D. The segments 34 and bends 36P, 36D are arranged in a zigzag pattern. The wire segments 34 preferably have the same length. In making the anchor a wire, so bent, is attached, as by welding, at its ends 32A, 32B to form a three-dimensional, generally tubular structure. The resulting anchor is resilient and can be compressed to a low profile, small diameter configuration suited for percutaneous delivery into the patient's vascular system.

In accordance with the invention, the anchor segments 34 are curved so that the anchor defines somewhat of an "hourglass" shape, having proximal and distal ends 35, 37 that define approximately the same diameter (when the anchor 30 is in its relaxed state) and a narrowed diameter waist portion 38.

Although the embodiment illustrated in FIG. 1 is shown as having a graft with an expanded diameter substantially corresponding to the diameter of the proximal and distal ends 35, 37 of the anchor, it is preferred to configure the anchor 30 and graft 20 so that the distal end of the anchor defines somewhat of a larger diameter. Thus, when the anchor 30 is used within the body, the proximal end 35 of the anchor 30 may expand the distal end of the graft to its open configuration and the distal end 37 of the anchor 30 may tend to extend radially outward as it extends from its proximal end 35 to its distal end 37, thereby assuring that the distal end of the anchor will engage the wall of the blood vessel.

The security of the engagement between the anchor 30 and the aorta wall may be further enhanced by hooks suggested diagrammatically at 40, which are secured to the anchor 30. The hooks 40, as suggested in FIG. 2, are formed on the distal ends of hook wire segments 42. The hook wire segments 42 preferably are formed from the same material as the main wire of the anchor 30. They are secured along the anchor segments 34, such that the hooks 40 are disposed beyond the distal bends 36D. The segments 42 are welded to the anchor segment 34 at first (proximal) and second (distal) junctions 46, 48. The hooks 40 preferably are sharp and aid in attaching the anchor 30 to the aorta wall to prevent migration after the device is implanted. It should be understood that although FIG. 1 illustrates a hook associated with each of the anchor segments 34, it may not be necessary to include a hook for each anchor segment.

Figure 3A:
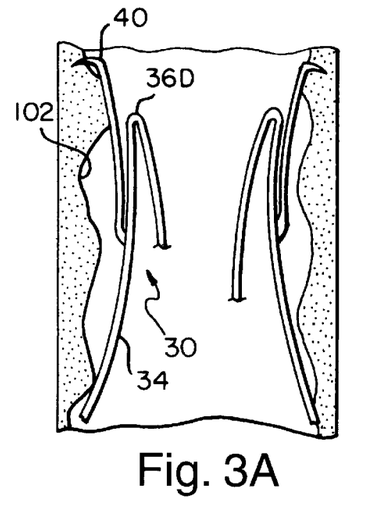
FIGS. 3A and 3B are, respectively, diagrammatic cross-sectional views of a curved anchor in accordance with the present invention contrasted with a straight stent within a vessel.
Figure 3B:
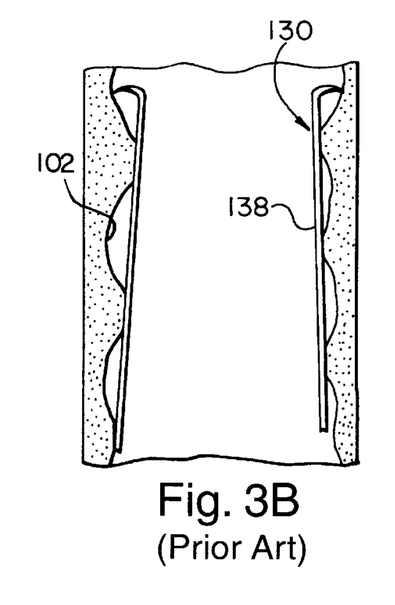

The curved configuration of the anchor segments serves several purposes. It results in a decrease in the surface area along which the anchor 30 engages the vessel wall. That, in turn, concentrates the resilient expansion force of the anchor at the point-like regions of contact of the bends 36P, 36D and hooks 40 so that they will tend to more firmly dig into and bear against the vessel wall. The anchor segment 34 may be curved to include an arc of between about 5° to about 30°. The effect of the curved configuration for the anchor segments may be seen from FIGS. 3A and 3B which show, diagrammatically, the contrast between the surface area of the anchor 130 in contact with the vessel wall 102 when a straight segment 138 (such as disclosed in the Gianturco patent) is used and the surface area of the anchor 30 in contact with the vessel wall 102 when a curved anchor segment 34 is used. As shown in FIG. 3B with an anchor having straight segments, the straight segments merely press flat against the vessel wall 102 and, even if provided with hooks, may not securely attach themselves to the vessel wall. Additionally, where, as is often the case, the inner luminal surface of the blood vessel may have irregularities, only portions of the straight segments may press against the high spots of the irregularities. In contrast, in the present invention, illustrated in FIG. 3A, the curved configuration of the wire segments 34 tends to space a major portion of the segments 34 from the wall of the blood vessel so that only the ends of the anchors will tend to engage the vessel wall. Consequently, the resilient force of expansion of the stent is concentrated in the ends of the anchor which enhances the attachment of the anchor in the blood vessel. Additionally, by concentrating the expansive force of the anchor at a plurality of relatively small area points, the device does not require an anchor having a high degree of spring expansile force. Thus, an anchor having a relatively weak spring force, but in which the force is focused on several relatively small areas, may be used. By using an anchor with a reduced level of expansile force, the risk of complications from the application of an excessive force on an already weakened artery wall is reduced.

Figure 4:
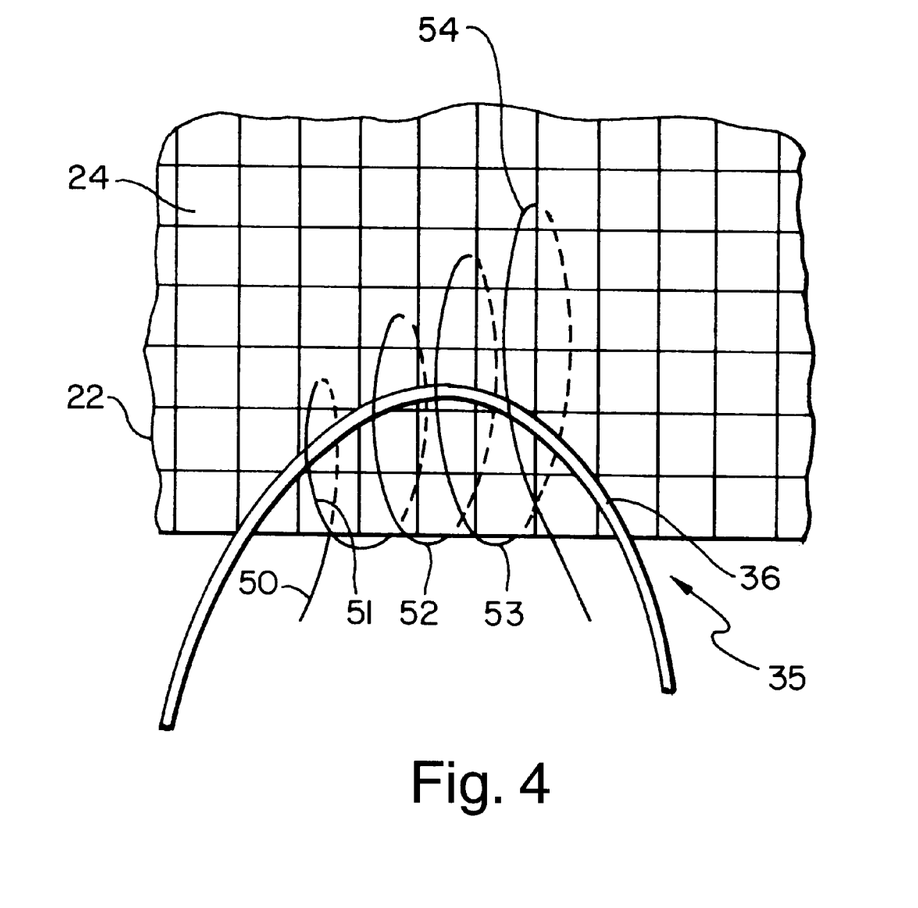
FIG. 4 is a detailed somewhat diagrammatic illustration of the attachment of the anchor, by sutures, to the graft.

The proximal end of the anchor 30 is secured to the distal end 22 of the graft 20. As shown in FIG. 4, the anchor 30 may be secured to the graft by suturing the proximal end of the anchor 30 to the distal end 22 of the graft 20. The suture 50 is passed through the mesh of the graft 20 and around the proximal bends 36P of the anchor 30. Preferably, the suture 50 is passed about the proximal bends 36P four times, with each successive stitch 51, 52, 53, 54 being further removed from the bend.

Another advantage of the anchor with curved wire segments is that the proximal end 35 of the anchor, when deployed in the patient, tends to merge smoothly with the body of the tubular graft to form a smooth transition and without any portion of the anchor protruding radially inwardly into the graft lumen. This is desirable particularly in those cases where a catheter may be inserted into the patient's vascular system in a subsequent procedure in which the catheter is passed through the graft. The existence of radially inwardly protruding portions of the anchor could present some risk of the catheter becoming caught on such protruding portion, thus risking injury to the patient, dislodgement of the graft as well as possible damage to the catheter. As shown in the embodiment of FIG. 1, it will be appreciated that the proximal ends of the anchor are attached directly to the distal end of the graft so that when deployed in the patient's blood vessel, the anchor will not have an inwardly protruding portion.

Figure 5:
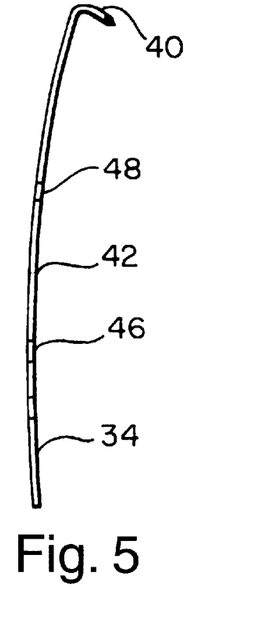
FIG. 5 is an illustration of a curved anchor segment and attached hook.
Figure 6:
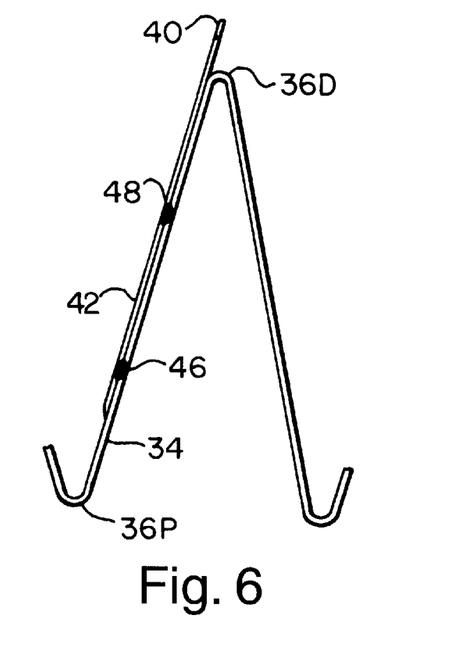
FIG. 6 is an illustration of a portion of the anchor as seen from the right of FIG. 5.

FIGS. 5 and 6 illustrate, in more representative detail the configuration of a segment 34 of an anchor in accordance with the invention. In this configuration, the wire segments 42 that support the hooks extend more fully toward the proximal bend 36P than in the configuration illustrated in FIGS. 1 and 2. By way of dimensional example, in an anchor adapted for use in an abdominal aortic aneurysm repair prosthesis, the length of the wire segments 34 that make up the anchor 30 may be of the order of 1.00 inches long. The hook wire segment 42 on which the hook 40 is formed may be of the order of ⅞ of an inch long with the hook 40 being disposed approximately ⅛ of an inch above the distal bend 34D associated with that hook. The wire from which the anchor and the hook segment are made may be of the order of 0.014 inches diameter. The proximal and distal resistance welds by which the hook segment is secured to the anchor segment may be disposed, respectively, ⅓ of an inch from the proximal bend 36P and about ¼ of an inch from the distal bend 36D. FIG. 5 illustrates a representative degree of curvature for the wire segment and an associated hook segment. By way of example, the degree of curvature may be of the order of 3 inches in radius. The expanded diameter of anchor 30 may be about 6 mm to 20 mm, depending on the diameter of the blood vessel, including a human aorta, into which it is placed.

Figure 7:
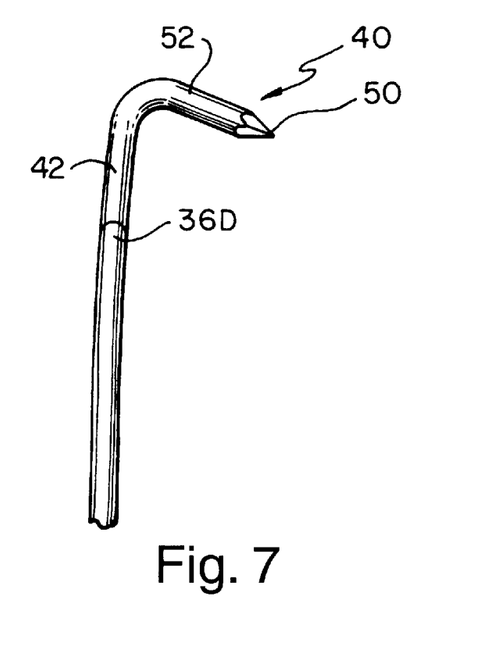
FIG. 7 is an enlarged illustration of the hook arrangement in FIG. 5.
Figure 8:
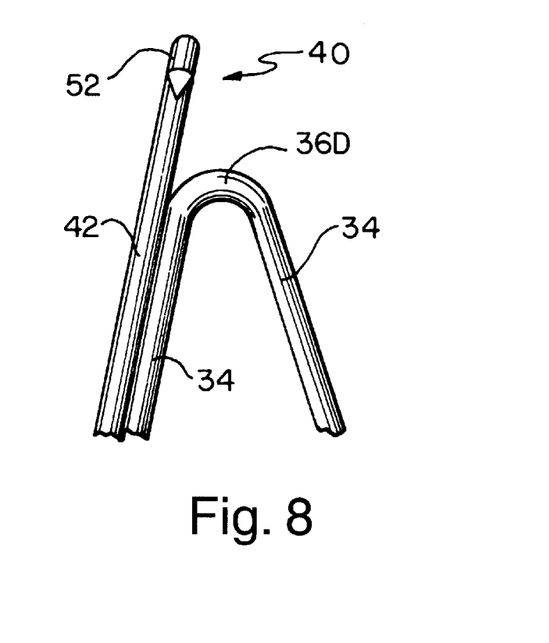
FIG. 8 is an enlarged illustration of the hook arrangement in FIG. 6.

FIGS. 7 and 8 illustrate in enlarged detail the configuration of a typical hook 40 and its associate distal bend 36D. The hook is provided with a sharpened tip 50 formed at the end of a generally radially outwardly protruding portion 52. The protruding portion which may be of the order of 0.050 inches long and may be formed by bending the hook wire 42 from which the hook is formed about a pin. The bends 36P, 36D may be formed by bending the wire about a pin.

Figure 9:
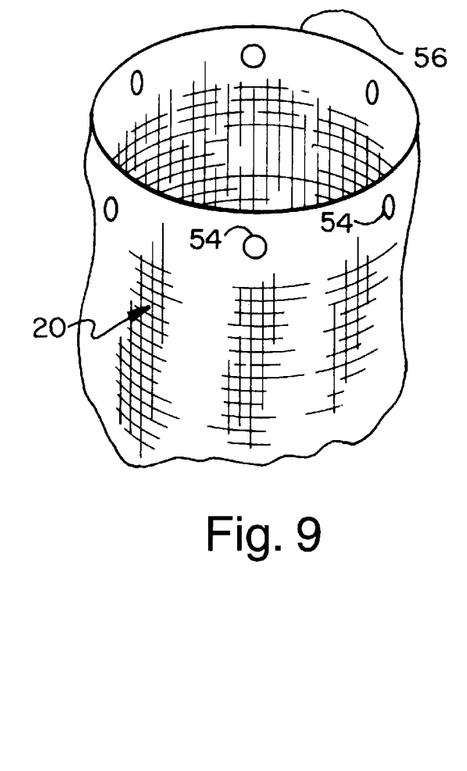
FIG. 9 is an illustration of the distal end of a graft having holes adapted to receive and be attached to an anchor.
Figure 10:
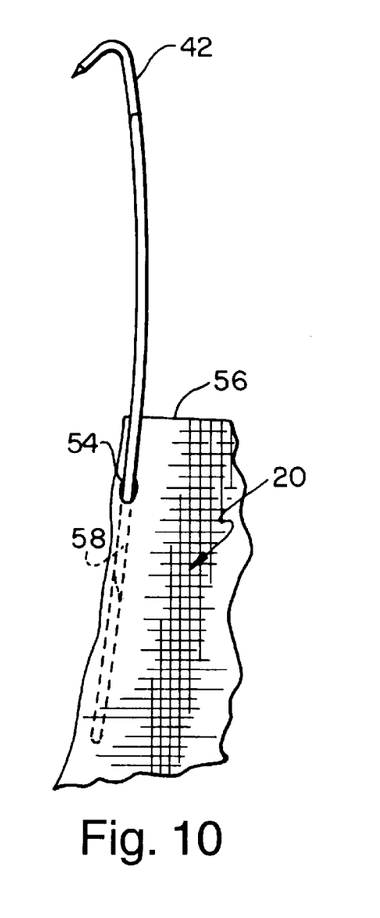
FIGS. 10 and 11 are illustrations of the manner in which an anchor may be attached to the graft as shown in FIG. 9.
Figure 11:
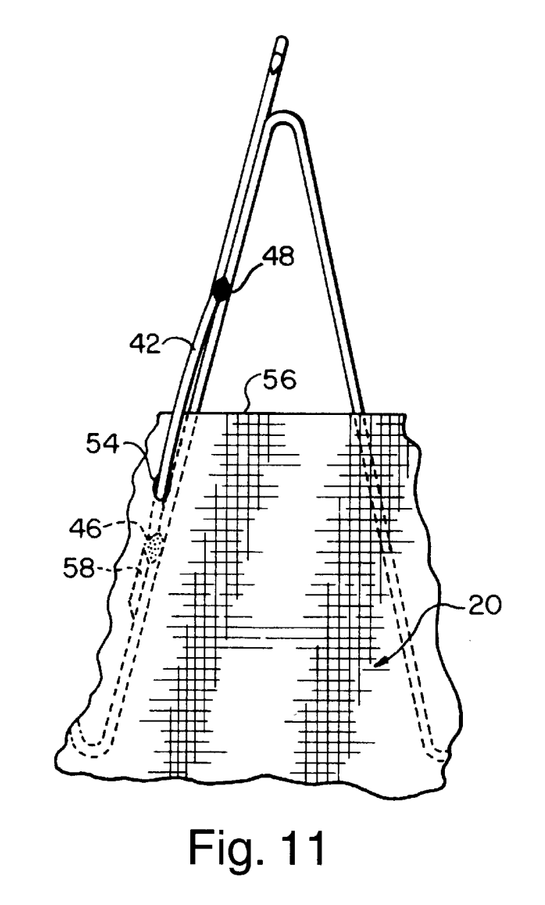

FIGS. 9, 10 and 11 illustrate portions of an assembly incorporating the anchor configuration of FIGS. 5–8 and an improved arrangement for attaching the graft 20 to the anchor 30. As shown in FIG. 9, the distal end of the graft 20 is formed to include a plurality of circumferentially spaced holes 54 disposed slightly proximally of the distal edge 56 of the graft. All edges of the graft including the distal edge 56 as well as the edges defined by the holes may be heat sealed or otherwise treated, if necessary, to prevent unraveling of the graft. By way of example, for an anchor 30 dimensioned as described above, the holes 54 may be of the order of 0.016 inches diameter and may be spaced approximately 2 mm from the distal edge 56 of the graft. FIGS. 10 and 11 illustrate the manner in which the anchor is attached to the graft. After the anchor 30 is formed as described above, the hook segment 42 is attached by resistance welding but only at one of the junctures 46, 48, preferably, the proximal juncture 46. When the desired number of hook segments 42 have been attached to the anchor segments 34, the proximal end 35 of the anchor is inserted into the distal end of the graft 20 but with the distal, unattached portion of the hook wire segment 42 overlying the outside of the distal margin of the graft and with its proximal end 58 passing inwardly through the hole 54 to the interior of the graft. With the graft and anchor so assembled, the distal resistance weld 48 may be made. Thus, the marginal portion of the graft is captured between the generally parallel anchor segments 34 and associated hook segments 42 between the proximal and distal junctures 46, 48. This arrangement is preferred to a sutured connection between the anchor and graft in that it cannot become unraveled and, additionally, is less bulky than the sutured connection.

In the preferred embodiment of the invention, the graft is selected so that when fully expanded, it will match or be slightly larger in diameter than the vessel to which it is to be implanted. It is intended that when the graft is deployed and expanded, the end of the graft will lie as close to the surface of the lumen of the blood vessel as possible in order to enhance tissue ingrowth into the graft wall and provide a smooth transition in the surface that defines the flow area from the healthy portion of the blood vessel into the graft. To that end, the anchor should be selected with respect to the graft so that the relaxed, freely expanded anchor will define a diameter slightly greater than the fully expanded diameter of the graft. That assures that when the device is deployed, the anchor will open the end of the graft fully.

Figure 12:
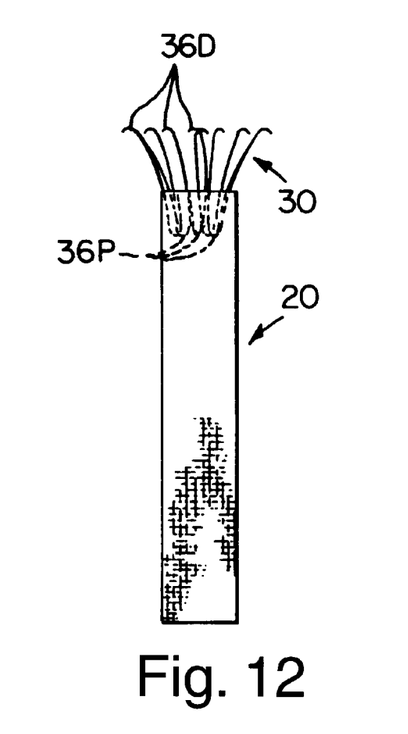
FIG. 12 is a diagrammatic illustration of a graft assembly with the distal anchor attached to the distal end of the graft and in a relaxed configuration.

FIG. 12 illustrates, diagrammatically, the configuration of the assembly when the graft 20 is attached to an anchor 30 as illustrated in FIGS. 9–11. When the graft 20 and attached anchor 30 are permitted to relax, the anchor assumes a distally flared configuration in which the bends 36D and hooks 40 at the distal end define a larger diameter than the inner end of the anchor that is disposed within the graft. In this configuration, the anchor biases the distal end of the graft in its open configuration. It should be understood, however, that when the device is actually deployed in the blood vessel, the segments of the anchor become aligned in generally parallel configuration and in which the proximal bends 36P of the anchor spread apart and lie closely against the inner surface of the graft as suggested in FIG. 13.

Figure 14:
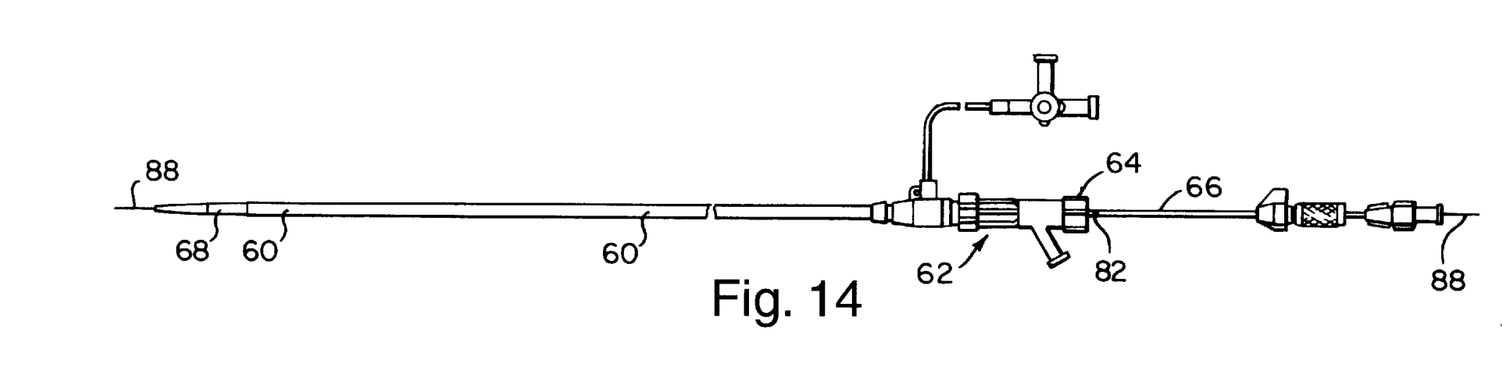
FIG. 14 is an illustration of the delivery device for the graft assembly.
Figure 15:
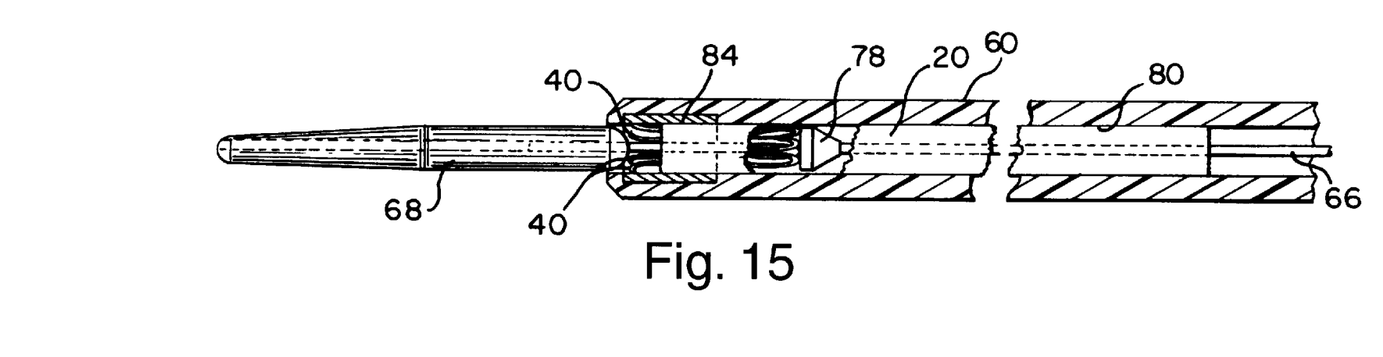
FIG. 15 is an enlarged sectional illustration of the distal region of the delivery device loaded with the graft assembly and in readiness for insertion into the patient.
Figure 16:
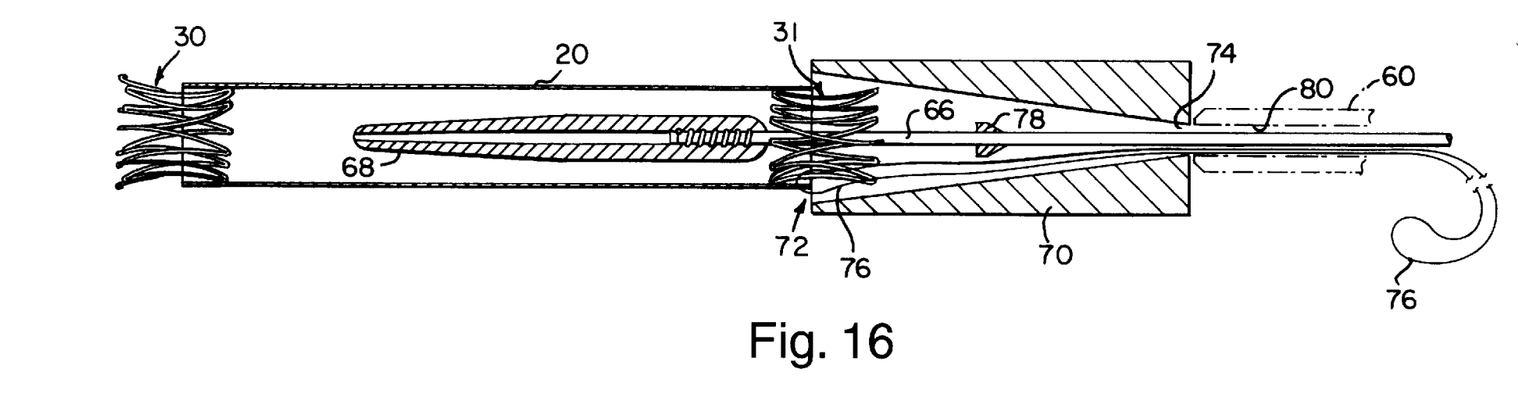
FIG. 16 is a diagrammatic illustration of the manner in which the graft assembly may be loaded into the distal end of the delivery device.

FIGS. 14–16 illustrate the catheter-like device by which the graft assembly may be percutaneously inserted and deployed within the patient's blood vessel. The delivery device includes an elongate flexible sheath 60 formed from a suitable polymeric material and having a fitting 62, including a Tuohy-Borst adapter 64 at its proximal end. The sheath 60 is adapted to receive a positioning tube 66 that has, at its distal tip, a flexible distally tapered dilator 68 and a stop member located proximally of the dilator tip. The proximal end 72 of the dilator tip is dimensioned to be received within the lumen 68 at the distal end of the flexible sheath. The tube 66 is longer than the sheath 60 so that when assembled, the proximal end of the tube 66 will protrude proximally of the Tuohy-Borst sheath adaptor 64. The positioning tube 66 is adapted to receive a guidewire to facilitate placement of the device.

When the delivery device and graft assembly are arranged in readiness for insertion into the patient, the graft assembly will be contained within the distal end of the sheath and about a portion of the positioning tube as illustrated in enlarged detail in FIG. 15. As suggested diagrammatically in FIG. 16, the graft assembly is loaded into the delivery device using a funnel-like loader 70 having an enlarged distal inlet end 72 and a narrowed proximal outlet end 74 (FIG. 16). The graft assembly is prepared for loading by attaching a long loop 76 of suture material to the proximal end of the graft. FIG. 16, which is diagrammatic and not to scale, illustrates the configuration of the delivery device when loading the graft assembly. The positioning tube 66 will have been extended through the sheath with its distal end extending beyond the distal tip of the sheath so that a step member 78 is spaced from the distal end of the sheath 60 by a distance greater than the length of the graft assembly 20, 30. The funnel 70 is disposed about the positioning tube 66 with the proximal end of the funnel being in communication with the distal outlet end of the sheath. The loop of suture 76 is passed through the funnel and along the lumen 80 of the sheath, exiting at the proximal fitting. The graft assembly is placed over the distal end of the positioning tube 66 in a position such that the proximal bends 36P of the distal anchor 30 are disposed distally of the stop 78. The graft assembly then is positioned on the tube 66 to locate the proximal bends adjacent the stop 78. With the elements so arranged, the positioning tube 66 and suture 76 are drawn together proximally to draw them through the funnel 70. As the positioning tube and graft assembly are drawn through the funnel 70, the graft is progressively constricted to a low profile about the positioning tube. By drawing them in unison, there is no relative lengthwise movement of the graft assembly with respect to the positioning tube. Consequently, as the graft assembly constricts about the positioning tube 66 and is drawn into the distal end of the sheath, the anchor is compressed to a low profile with its proximal bends 36P bearing against the distal face of the stop 78. The tube 66 preferably is provided with a marker 82 (FIG. 14) near its proximal end, the marker being located so that when it is exposed proximally of the fitting 62, the graft assembly will have been withdrawn fully into the distal end of the sheath and the proximal end of the dilator tip also is drawn slightly into the distal tip of the sheath, as shown in FIG. 15. The distal tip of the sheath preferably is provided with an inner lining segment 84 formed from a relatively hard material. The lining segment is dimensioned and located to be aligned with the hooks on the distal end of the distal anchor and serves to prevent the hooks 40 from digging into the softer material from which the sheath is formed. Additionally, the distal liner preferably is formed from a material sufficiently dense to be observed under fluoroscopy. When the device is thus loaded, the proximally extending suture 76 may be cut and pulled out of the device. The device then is in readiness for insertion into the patient and deployment of the graft assembly.

In the preferred embodiment, the graft assembly is provided with an additional anchor suggested diagrammatically at 31 in FIG. 16. The proximal anchor 31 is desirable in order to stabilize the proximal end of the graft and maintain it in a fully opened position as well as to maintain the graft in contact with the blood vessel wall to provide tissue ingrowth. No hooks are required in connection with the proximal anchor 31.

Figure 13:
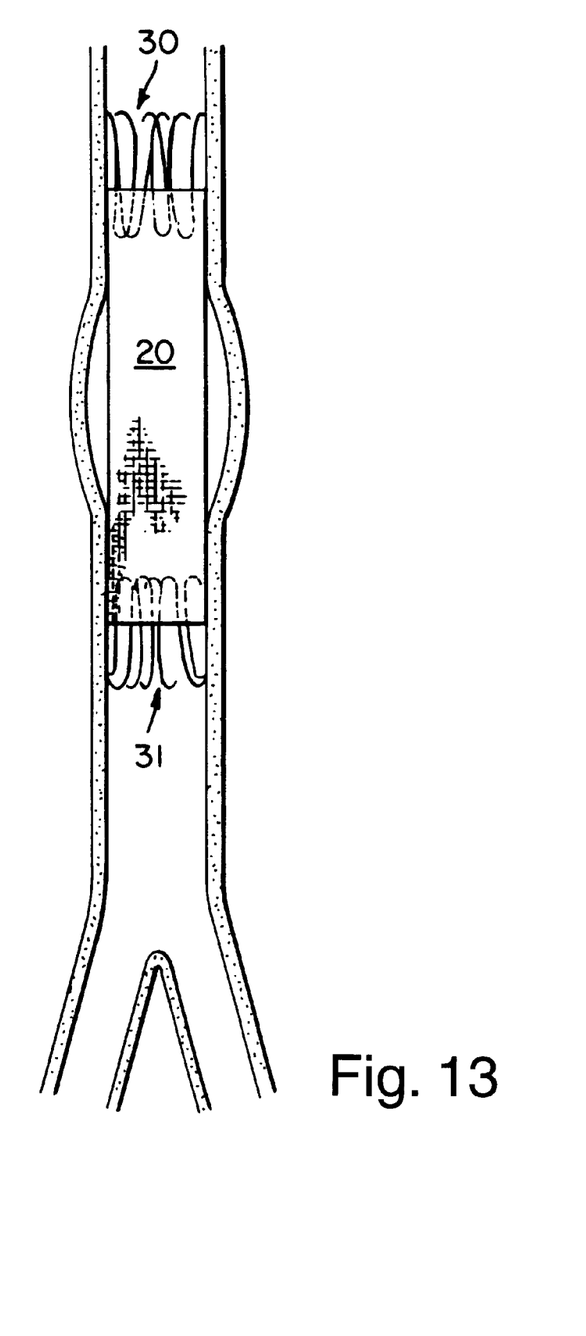
FIG. 13 is an illustration of a graft in accordance with the invention implanted in the aorta so that the graft spans an aortic aneurysm.

The device is inserted percutaneously into the patient's vasculature with the aid of a guidewire. The guidewire 88 may be preliminarily loaded into the lumen of the positioning tube before the delivery device is inserted into the patient or, alternately, the guidewire may be placed separately in a preliminary procedure into the patient's blood vessel. In either case, the delivery device is advanced into the patient's blood vessel, for example, as through the femoral artery when placing a graft assembly to treat an abdominal aneurysm. The guidewire may be advanced independently toward and through the region to be treated. The delivery assembly then may be advanced over the guidewire until the graft assembly is in its intended position. In the case of an abdominal aortic aneurysm, the device would be located so that the distal anchor is located distally of the region of the aneurysm such that the graft, when deployed, can pass through the aneurysm thereby lining the artery. With the delivery device so placed, the position of the positioning tube is maintained while the sheath is withdrawn in a proximal direction. The stationary stop maintains engagement with the proximal ends of the distal anchor thereby preventing proximal movement of the graft assembly while the sheath is withdrawn. As the sheath is progressively withdrawn and the anchor emerges from the distal end of the sheath, the anchor expands into engagement with the inner luminal surface of the blood vessel while simultaneously expanding the distal end of the graft. FIG. 13 illustrates the configuration of the expanded, deployed anchor region from which it may be seen that the proximal ends of the anchor 30 lie firmly against the graft material and, optimally, press the graft at a plurality of discrete regions against the wall of the blood vessel. The hooks at the distal end of the distal anchor embed themselves in the wall of the blood vessel under the influence of the inherent resilience of the anchor. As the sheath is progressively withdrawn, the proximal anchor, if used, also emerges from the sheath and expands into engagement with the blood vessel.

It should also be appreciated that the scope of the invention is not confined to the specific embodiments illustrated and described herein. Rather, it is the intention of the applicant that the scope of the invention be determined by the appended claims and their equivalents.

We claim:

1. A vascular repair assembly adapted to inhibit migration of the assembly once it is positioned within a blood vessel, comprising:

an elongate tubular graft having a proximal end and a distal end;

a fixed length self-expanding anchor having a proximal end, a distal end and an intermediate portion defined by a plurality of generally longitudinally extending curved anchor segments, the anchor being secured to the distal end of the graft, each of the anchor segments extending substantially the full length of the anchor;

the curve of the anchor segments being oriented radially outwardly toward each of the proximal and distal ends of the anchor so that both the distal and proximal ends of the anchor define diameters greater than that of the intermediate portion.

2. A repair assembly according to claim 1, wherein said anchor has a tubular shape with a longitudinal axis and has a diameter which varies along said longitudinal axis.

3. A repair assembly according to claim 2, wherein said anchor comprises a single, continuous wire which includes a series of bends, the anchor segments being defined by those portions of the wire that extend between the bends.

4. A repair assembly according to claim 2, wherein at least one hook is secured adjacent said distal end of said anchor.

5. A repair assembly according to claim 2, wherein said distal end and said proximal end of said anchor have the same diameter which is larger than a diameter of said intermediate portion of said anchor.

6. A repair assembly according to claim 1, wherein said anchor comprises a single, continuous wire.

7. A repair assembly according to claim 6, wherein said single wire includes a series of bends and radially outwardly curved anchor segments connecting sequential bends in said series of bends, and said wire has first and second ends that are joined together to form a three-dimensional structure having a generally tubular shape.

8. A repair assembly according to claim 7, wherein said anchor has a longitudinal axis, and said radially outwardly curved anchor segments are oriented such that the diameter of said anchor varies along said longitudinal axis.

9. A repair assembly according to claim 8, wherein said distal end and said proximal end of said anchor have the same diameter which is larger than a diameter of said intermediate portion of said anchor.

10. A repair assembly according to claim 6, wherein said wire is metal.

11. A repair assembly according to claim 1, wherein said distal end of said graft is secured to said anchor adjacent said proximal end of said anchor.

12. A repair assembly according to claim 1, wherein at least one hook is secured adjacent said distal end of said anchor.

13. A method for repairing injured blood vessels comprising the steps of:

attaching a self expanding anchor to a distal end of a graft;

positioning said anchor and said graft at a predetermined location within a blood vessel; and securing said anchor within said blood vessel such that migration of said graft is prevented;

wherein said anchor comprises;

a generally tubular fixed length structure formed from a plurality of fixed length radially outwardly curved anchor segments which extend from the proximal end of said anchor to the distal end of said anchor, the proximal and distal ends of the anchor defining a plurality of circumferentially spaced anchor regions disposed about circles, each of which has a greater diameter than the diameter defined by the midportion of the anchor as the result of the curvature of the anchor segments, the number of the circumferentially spaced anchor regions being selected to focus the radially outward pressure applied by the self expanding anchor against the blood vessel wall to a small number of points along the circle.

14. A method according to claim 13, wherein said anchor comprises a single, continuous wire.

15. A method according to claim 14, wherein said single wire includes a series of bends and radially outwardly curved anchor segments extending between adjacent of said bends, and said wire has first and second ends that are joined together to form a three-dimensional structure having a generally tubular shape.

16. A method according to claim 15, wherein said anchor has a longitudinal axis, and said radially outwardly curved anchor segments are oriented such that the diameter of said anchor varies along said longitudinal axis.

17. A method according to claim 13, wherein said anchor has a tubular shape with a longitudinal axis and has a diameter which varies along said longitudinal axis.

18. A method according to claim 13, wherein said distal end of said graft is secured to said anchor adjacent said proximal end of said anchor.

19. A method according to claim 13, wherein said anchor includes at least one hook segment secured adjacent said distal end of said anchor and having a proximal extension thereof, and wherein said distal end of said graft includes at least one hole;

and, wherein said proximal extension of said at least one hook segment projects through said at least one hole, securing said anchor to said graft.

20. A repair assembly for placement in a patient's vascular system comprising:

a graft having a proximal end, a distal end and a generally tubular shape, said graft having at least one hole through a sidewall proximate to the distal end;

a self expanding anchor having a body and at least one hook segment extending from said body at a first location;

wherein said at least one hook segment extends through said hole in said graft and along the graft toward the distal end so that said distal end and a portion of said sidewall of said graft are captured between said hook segment and said body;

wherein said at least one hook segment is attached to said body at a second location so that said distal end and a portion of said sidewall are positioned between said first and second attachment locations.

21. The repair assembly recited in claim 1 wherein said anchor is resilient and said radially outwardly curved intermediate portion concentrates said resiliency at said proximal and distal ends of said anchor.

* * * * *